US012693276B2

(12) United States Patent
Sato et al.

(10) Patent No.: US 12,693,276 B2
(45) Date of Patent: Jul. 28, 2026

(54) METHOD FOR DETERMINING ORIGIN OF CARBON SOURCE OF CHEMICAL SUBSTANCE

(71) Applicant: SEKISUI CHEMICAL CO., LTD., Osaka (JP)

(72) Inventors: Kanetomo Sato, Tokyo (JP); Norio Numata, Tokyo (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 344 days.

(21) Appl. No.: 17/624,396

(22) PCT Filed: Jul. 3, 2020

(86) PCT No.: PCT/JP2020/026297
§ 371 (c)(1),
(2) Date: Jan. 3, 2022

(87) PCT Pub. No.: WO2021/006226
PCT Pub. Date: Jan. 14, 2021

(65) Prior Publication Data
US 2022/0334093 A1    Oct. 20, 2022

(30) Foreign Application Priority Data

Jul. 5, 2019    (JP) ................................. 2019-126293

(51) Int. Cl.
*G01N 30/88*        (2006.01)
*G01N 33/44*        (2006.01)
(52) U.S. Cl.
CPC ........... *G01N 30/88* (2013.01); *G01N 33/442* (2013.01); *G01N 2030/8809* (2013.01)
(58) Field of Classification Search
CPC ................. G01N 30/88; G01N 33/442; G01N 2030/8809
See application file for complete search history.

(56) References Cited

U.S. PATENT DOCUMENTS

2016/0046871 A1    2/2016  Huber et al.
2016/0122869 A1*   5/2016  Lei .......................... C23C 16/36
                                                         546/14
(Continued)

FOREIGN PATENT DOCUMENTS

JP        2005-17018        1/2005
JP        2006-90866        4/2006
(Continued)

OTHER PUBLICATIONS

International Search Report (ISR) issued Sep. 24, 2020 in International (PCT) Application No. PCT/JP2020/026297.
Ploykrathok, T. et al., "Determining the bio-based content of bio-plastics used in Thailand by radiocarbon analysis", Journal of Physics: Conference Series, Jun. 1, 2017, vol. 860, pp. 1-7.
(Continued)

*Primary Examiner* — Shelby A Turner
*Assistant Examiner* — Xiuqin Sun
(74) *Attorney, Agent, or Firm* — Wenderoth, Lind & Ponack, L.L.P.

(57)        ABSTRACT

Provided is a method for determining origin of carbon source of chemical substance, which makes it possible to determine whether resource-recycled carbon is used as a carbon raw material from a chemical substance in various goods. The method for determining origin of carbon source of chemical substance includes: a step S1 of acquiring a carbon-14 content rate $R_1$ of a standard chemical substance having carbon element in which carbon has been recycled as a resource; a step S2 of acquiring a carbon-14 content rate $R_2$ of a chemical substance to be identified; a step S3 of calculating a ratio $(R_2/R_1)$ of the content rate $R_2$ to the content rate $R_1$; and a step S4 of determining that a carbon raw material in the chemical substance to be identified contains resource-recycled carbon based on the ratio $(R_2/R_1)$.

11 Claims, 1 Drawing Sheet

(56) References Cited

U.S. PATENT DOCUMENTS

| | | | |
|---|---|---|---|
| 2016/0349177 A1* | 12/2016 | Iguchi | ................ G01N 21/3504 |
| 2020/0062915 A1* | 2/2020 | Ramesh | ................ C08J 9/0095 |

FOREIGN PATENT DOCUMENTS

| | | | |
|---|---|---|---|
| JP | 2006090866 A | * | 4/2006 |
| JP | 2007-45857 | | 2/2007 |
| JP | 2007-85874 | | 4/2007 |
| JP | 2009-128283 | | 6/2009 |
| JP | 2013-504651 | | 2/2013 |
| JP | 2014-88349 | | 5/2014 |
| JP | 2014-166622 | | 9/2014 |
| JP | 2017-15503 | | 1/2017 |
| JP | 2017-87210 | | 5/2017 |
| WO | 2012/004457 | | 1/2012 |

OTHER PUBLICATIONS

Taguchi, Kazuhiro et al., "Biobased carbon content of resin extracted from polyethylene composite by carbon-14 concentration measurements using accelerator mass spectrometry", SpringerPlus, Dec. 1, 2014, vol. 3, No. 1, pp. 1-11.

Hooijmans, J.W. et al., "Open-Bio Opening bio-based markets via standards, labelling and procurement: Evaluation of applicable techniques for the determination of the bio-based content", Work Package 3: Bio-based content, Dec. 1, 2015, pp. 1-30.

Saito, M., et al., "A Specification of Bio-Fuel by Easy C-14 Measurement," Bulletin of Tokyo Metropolitan Industrial Technology Research Institute, Tokyo Metropolitan Industrial Technology Research Institute, non-official translation (Biofuel origin determination technology using natural radiocarbon C-14), pp. 16-19, 2009 (cited in ISR and English Abstract) (4 pages).

Office Action issued Apr. 21, 2026, in Japanese Patent Application No. 2025-033011, with English translation.

* cited by examiner

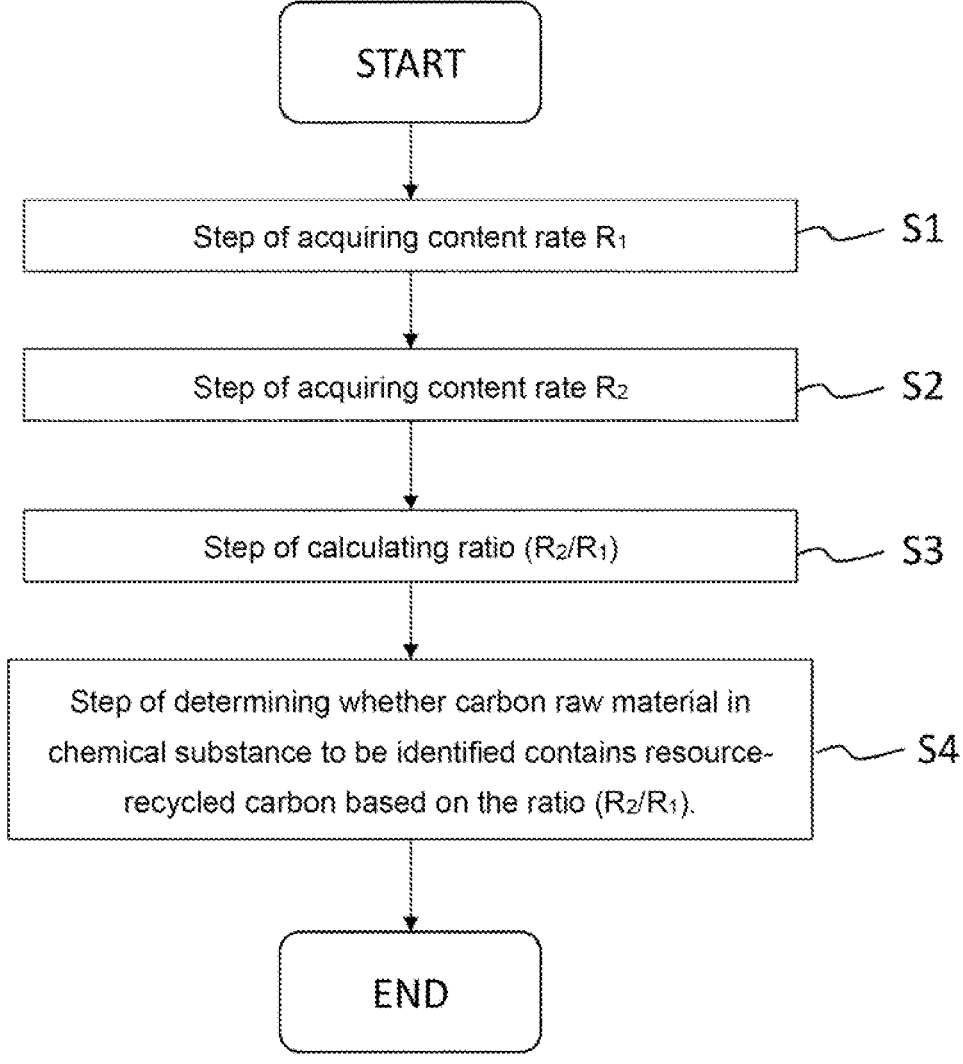

METHOD FOR DETERMINING ORIGIN OF CARBON SOURCE OF CHEMICAL SUBSTANCE

TECHNICAL FIELD

The present invention relates to a method for determining origin of carbon source of chemical substance and particularly to a method for determining the origin of a chemical substance in a carbon raw material to determine whether carbon has been recycled as a resource.

BACKGROUND ART

In recent years, there has been a growing demand for methods to produce various organic substances from raw materials other than fossil fuel resources, from the viewpoint of the threat of depletion of fossil fuel resources and the global environmental problem of an increase in carbon dioxide in the atmosphere. As a method for producing various organic substances from raw materials other than fossil fuel resources, for example, a method for producing biomass-derived ethanol from biomass resources by a sugar fermentation method has been drawing attention. In the sugar fermentation method using biomass resources which are edible raw materials such as corn, however, the limited area of agricultural land is used for production other than food, thereby causing problems such as soaring food prices, and thus there is a need to use raw materials that do not compete with food. From the viewpoint of environmental problems, there is a need to use recycled raw materials that do not use any additional resources such as fossil fuel resources and biomass resources.

In order to meet such demands, a method of using waste as a recycled raw material to produce chemical substances that were previously produced by fossil fuel resource has been studied. Specifically, a method for producing ethanol by microbial fermentation from synthesis gas or the like obtained by gasification of waste has been proposed (see, for example, PTL1).

The waste-derived ethanol described above is expected to have the least impact on the global environment because it uses carbon derived from recycled raw materials (waste) that have been recycled without using any additional resources as carbon raw materials.

CITATION LIST

Patent Literature

PTL1: JP 2007-45857 A

SUMMARY OF INVENTION

Technical Problem

The consumers of chemical substances such as general consumers and companies have been increasingly interested in environmental problems over the years, and thus more and more of them are actively purchasing goods made from chemical substances containing resource-recycled carbon. Therefore, it is considered that suppliers may actively display the use of resource-recycled carbon as the carbon raw materials for each of their goods in order to respond to consumers' purchase intention. However, it is difficult to determine whether resource-recycled carbon is used as a carbon raw material for goods made from chemical substances, and it is considered necessary to have a system to inspect whether the display of the use of resource-recycled carbon is appropriate.

The present invention is made in consideration of the above issue and aims to provide a method for determining origin of carbon source of chemical substance, which makes it possible to determine whether resource-recycled carbon is used as a carbon raw material from chemical substances in various goods.

Solution to Problem

As a result of intensive study to solve the above issue, the present inventors found that it is possible to determine whether a carbon raw material in a chemical substance is resource-recycled carbon by using the ratio of a carbon-14 ($^{14}$C) content rate of the chemical substance to a carbon-14 content rate of a standard chemical substance produced by resource-recycled carbon, and completed the following invention.

Thus, the present invention provides the following [1] to [10].

[1] A method for determining origin of carbon source of chemical substance, comprising: a step of acquiring a carbon-14 content rate $R_1$ of a standard chemical substance having carbon element in which carbon has been recycled as a resource; a step of acquiring a carbon-14 content rate $R_2$ of a chemical substance to be identified; a step of calculating a ratio ($R_2/R_1$) of the content rate $R_2$ to the content rate $R_1$; and a step of determining that a carbon raw material in the chemical substance to be identified contains resource-recycled carbon based on the ratio ($R_2/R_1$).

[2] The method for determining origin of carbon source of chemical substance according to [1], wherein in the step of determining, the carbon raw material in the chemical substance to be identified is determined as resource-recycled carbon when the ratio ($R_2/R_1$) is 0.5 or more and 2.0 or less.

[3] The method for determining origin of carbon source of chemical substance according to [1] or [2], wherein in the step of determining, the carbon raw material in the chemical substance to be identified is determined as resource-recycled carbon when the ratio ($R_2/R_1$) is 1.0.

[4] The method for determining origin of carbon source of chemical substance according to any one of [1] to [3], wherein the standard chemical substance is ethanol.

[5] The method for determining origin of carbon source of chemical substance according to any one of [1] to [4], wherein the chemical substance to be identified is one chosen from the group consisting of ethylene and polyethylene resins.

[6] The method for determining origin of carbon source of chemical substance according to any one of [1] to [5], wherein the content rate $R_1$ is an average value of carbon-14 content rates of a plurality of standard chemical substances.

[7] The method for determining origin of carbon source of chemical substance according to [6], wherein the average value of carbon-14 content rates of a plurality of the standard chemical substances is an average value of carbon-14 content rates of the standard chemical substances produced at a plurality of sites.

[8] The method for determining origin of carbon source of chemical substance according to [6] or [7], wherein the average value of carbon-14 content rates of a plurality of the standard chemical substances is an average value of carbon-14 content rates of the standard chemical substances produced in a plurality of times. [9] The method for determining origin of carbon source of chemical substance according to any one of [1] to [5], wherein the content rate $R_1$ is a carbon-14 content rate of each production lot in which the standard chemical substance is produced from resource-recycled carbon.

[10] The method for determining origin of carbon source of chemical substance according to any one of [1] to [9], comprising a step of calculating $[100-|(R_2/R_1)-1|\times100]$ (%) as a usage rate of the resource-recycled carbon.

Advantageous Effects of Invention

According to the present invention, it is possible to provide a method for determining origin of carbon source of chemical substance, which makes it possible to determine whether resource-recycled carbon is used as a carbon raw material from a chemical substance in various goods.

BRIEF DESCRIPTION OF DRAWING

FIG. 1 is a flowchart showing a method for determining the origin of carbon raw materials according to embodiments of the present invention.

DESCRIPTION OF EMBODIMENTS

Hereinafter, the present invention will be described through embodiments of the invention, but the following embodiments do not limit the invention within the scope of the claims. In addition, not all of the combinations of features described in the embodiments are essential to the solution of the invention.

Method for Determining Origin of Carbon Source of Chemical Substance

The method for determining origin of carbon source of chemical substance according to an embodiment of the present invention, as shown in FIG. 1, includes: a step S1 of acquiring a carbon-14 content rate $R_1$ of a standard chemical substance having carbon element in which carbon has been recycled as a resource; a step S2 of acquiring a carbon-14 content rate $R_2$ of a chemical substance to be identified; a step S3 of calculating a ratio $(R_2/R_1)$ of the content rate $R_2$ to the content rate $R_1$; and a step S4 of determining that a carbon raw material in the chemical substance to be identified contains resource-recycled carbon based on the ratio $(R_2/R_1)$.

<Step of Acquiring Content Rate $R_1$>

In the step S1, a carbon-14 content rate $R_1$ of a standard chemical substance comprising carbon in which a carbon element has been recycled as a resource is acquired.

In the present specification, the term "standard chemical substance" refers to a chemical substance made from carbon elements in which all carbon have been recycled as resources and generated from waste-derived gas obtained, for example, by burning and thermally decomposing recycled raw materials (waste).

Examples of the standard chemical substance include ethanol and ethylene. Among them, ethanol is preferable from the viewpoint of availability as a raw material for a variety of chemical substances and ease of generation from waste.

The term "ethanol" used herein as a standard chemical substance means not only pure ethanol (ethanol represented by the chemical formula: $CH_3CH_2OH$) as a compound but also a composition containing impurities (admixture components) inevitably contained in ethanol produced through synthesis or purification. The same applies to other substances such as "ethylene" used as a standard chemical substance.

The recycled raw materials (waste) may be industrial waste such as industrial solid waste or general waste such as municipal solid waste (MSW), and include flammable substances such as plastic waste, garbage, waste tires, biomass waste, food waste, construction materials, wood, wood chips, fibers, and paper. Among these, municipal solid waste (MSW) is preferable.

The carbon-14 content rate $R_1$ of a standard chemical substance made from resource-recycled carbon is an amount of carbon-14 in the standard chemical substance with respect to the total amount of carbon in the standard chemical substance, as shown in the following formula.

$$\text{Content rate } R_1(\%)=(\text{Amount of carbon-14 in standard chemical substance/Total amount of carbon in standard chemical substance})\times100$$

Methods for acquiring the content rate $R_1$ of a standard chemical substance include liquid scintillation measurement counting, gas proportional counting, and accelerator mass spectrometry, and among them, liquid scintillation counting is preferable from the viewpoint of operability, ease of correction, and high accuracy.

Note that the carbon-14 content rate $R_1$ of a standard chemical substance can be expressed by a PMC (Percentage of Modern Carbon) value, which is a carbon-14 concentration when a carbon concentration in 1950 is 100, for example.

The carbon-14 content rate $R_1$ of a standard chemical substance depends on resource-recycled carbon used as its raw material and matches a carbon-14 content rate of the resource-recycled carbon. The carbon-14 content rate of the resource recycled carbon depends on a recycled raw material (waste) and matches a carbon-14 content rate of the carbon elements contained in the recycled raw material (waste). If society becomes completely resource-recycling-oriented in the future, in which 100% of recycled raw materials (waste) are used to produce chemical substances, the recycled raw materials (waste) containing carbon elements with a constant carbon-14 content rate will be recycled, resulting in the carbon-14 content rate $R_1$ of a standard chemical substance converging to a constant value. In other words, if the society becomes completely resource-recycling-oriented, the carbon-14 content rate $R_1$ of a standard chemical substance will be a constant value, and thus such value will be adopted.

At present, the society is not yet completely resource-recycling-oriented, and the carbon-14 content rate $R_1$ of standard chemical substances has not yet reached a certain value, and thus the content rate $R_1$ varies with differences in types of the waste in different regions, differences in types of the waste in each manufacturing plant, and the like. Accordingly, it is preferable to use a chemical substance actually produced from recycled raw materials (waste) at a manufacturing plant as a standard chemical substance and adopt a carbon-14 content rate of the standard chemical substance as the carbon-14 content rate $R_1$ of the standard chemical substance.

In addition, it is considered that the resource-recycling-oriented society is currently in the process of progressing and that the content rate $R_1$ is in the process of converging to a certain value as described above, and therefore it is more preferable to use chemical substances that have been recently produced from recycled raw materials (waste) at a manufacturing plant as the standard chemical substances.

It is also preferable to adopt, for example, an average value of the carbon-14 content rates of a plurality of standard chemical substances as the carbon-14 content rate $R_1$ of the standard chemical substance.

In a case where the average value of carbon-14 content rates of a plurality of the standard chemical substances is adopted, it is preferable to use the average value of carbon-14 content rates of the standard chemical substances comprising resource-recycled carbon is preferably at a plurality of sites for the means of acquiring the average value.

Generally, there are a plurality of manufacturing plants where chemical substances are produced from recycled raw materials (waste), but the carbon-14 content rate of chemical substances obtained in each manufacturing plant may differ due to regional differences. Therefore, it is possible to reduce the bias in the content rate $R_1$ due to regional differences by using the average value of carbon-14 content rates of standard chemical substances, which comprise resource-recycled carbon, obtained at a plurality of sites.

Note that the manufacturing plants at a plurality of sites may be a plurality of sites in the same region (for example, within the same prefecture, within the same commercial zone), within the same country (for example, Japan), and within the same area (for example, European Union), or may be within the entire world. For example, if the carbon-14 content rate of a standard chemical substance is obtained at a plurality of sites within the same country and the average value is calculated, it is useful to determine whether the chemical substance produced within the country is derived from resource-recycled carbon.

It is also preferable to adopt the average value of carbon-14 content rates of standard chemical substances, which comprise resource-recycled carbon, obtained in a plurality of times as the carbon-14 content rate $R_1$ of the standard chemical substance. Here, the standard chemical substances obtained in a plurality of times are those obtained at the same sites (in other words, the same manufacturing plant). The content rate $R_1$ is an average value of the carbon-14 content rates of standard chemical substances, which comprise resource-recycled carbon, obtained at a plurality of sites, thereby making it possible to reduce the bias in the content rate $R_1$ that depends on the type of waste at each chronologically different time when resource-recycled carbon is obtained in the same manufacturing plant.

Note that generally when chemical substances are produced from recycled raw materials (waste) in each of the plants, lots are often assigned chronologically. Therefore, the average value of carbon-14 in standard chemical substances of a plurality of lots may be used as the content rate $R_1$. For example, if the carbon-14 content rate of standard chemical substances of a plurality of lots is obtained and the average value is calculated, it is useful to determine whether the chemical substances produced in a plurality of lots are derived from resource-recycled carbon.

It is also preferable to adopt the average value of carbon-14 content rates of standard chemical substances, which comprise resource-recycled carbon, obtained at a plurality of sites over a plurality of times as the carbon-14 content rate $R_1$ of the standard chemical substance. The content rate $R_1$ is an average value of the carbon-14 content rates of standard chemical substances, which comprise resource-recycled carbon, obtained at a plurality of sites over a plurality of times, thereby making it possible to reduce the bias in the content rate $R_1$ due to regional differences and the bias in the content rate $R_1$ due to chronological differences.

For example, the carbon-14 content rate of each production lot in which the standard chemical substance is produced from resource-recycled carbon may be adopted as the carbon-14 content rate $R_1$ of the standard chemical substance. The carbon-14 content rate of standard chemical substances of each production lot is used as the content rate $R_1$, thereby making it possible to identify the carbon-14 content rate of the standard chemical substance obtained in each of the production lots, and the carbon-14 content rate of the standard chemical substance is compared with carbon-14 content rates of chemical substances in various goods to detect those that match, thereby making it possible to track which production lot the standard chemical substances were obtained in.

The carbon-14 content rate $R_1$ of standard chemical substances as described above can be taken from a variety of viewpoints, and these may be adopted alone or in combination.

<Step of Acquiring Content Rate $R_2$>

In the step S2, a carbon-14 content rate $R_2$ of a standard chemical substance to be identified is acquired.

The chemical substance to be identified is not limited as long as it is an organic compound. The form of the chemical substance to be identified is not limited and may be the chemical substance itself or a mixture of the chemical substance to be identified and other chemical substances. Such other chemical substances may be inorganic substances or organic compounds other than the chemical substance to be identified. The chemical substance to be identified may be a single chemical substance alone or two or more chemical substances to be identified.

In addition, the chemical substance to be identified may be a chemical substance that has undergone various processing. Specifically, it may be an article made from the chemical substance to be identified or may be an article of a composition containing the chemical substance to be identified and other chemical substances.

Examples of the article include a film, a sheet, a thin-walled molded article, and a hollow molded article. Examples of methods for molding articles include injection molding, blow molding, extrusion molding, compression molding, stretch molding, vacuum forming, internal pressure molding, and tearing molding.

When mixed with other chemical substances, the chemical substance to be identified may be separated from the other chemical substances.

Specific examples of the chemical substance to be identified are not limited as long as it can be composed of resource-recycled carbon and include ethanol, ethylene, a polymer having a constituent unit derived from ethylene such as a polyethylene resin, butadiene, ethylene, propylene, isobutene, acetaldehyde, acetic acid, ethyl acetate, methyl (meth)acrylate, ethyl-t-butyl ether ethylene glycol, an ester composition, an acrylic acid, an aminohexanoic acid, diethyl carbonate, a polyester resin, a polyethylene resin (PE), a polyethylene terephthalate resin (PET), a polypropylene resin (PP), a polyisobutylene resin, a polymethyl methacrylate resin (PMMA), ethylene-propylene-diene rubber (EPDM), a polybutylene terephthalate resin (PBT), a polyethylene furanoate resin (PEF), and polyurethane resin (PU). The chemical substance to be identified is preferably one chosen from the group consisting of ethylene and polyethylene resins from the viewpoint of availability and versatility.

The carbon-14 content rate $R_2$ of a chemical substance to be identified is an amount of carbon-14 in the chemical substance to be identified, with respect to the total amount of carbon in the chemical substance to be identified, as shown in the following formula.

Content rate $R_2$(%)=(Amount of carbon-14 in chemical substance to be identified/Total amount of carbon in standard chemical substance to be identified)×100

A similar method for acquiring the carbon-14 content rate $R_1$ of the standard chemical substances described above can be adopted as the method for acquiring the carbon-14 content rate $R_2$ of chemical substances to be identified.

<Step of Calculating Ratio ($R_2/R_1$)>

In the step S3, a ratio ($R_2/R_1$) of the content rate $R_2$ to the content rate $R_1$ is calculated.

The ratio ($R_2/R_1$) is calculated using the content rate $R_1$ acquired in the step S1 and the content rate $R_2$ acquired in the step S2.

<Step of Determining>

In the step S4, a carbon raw material in a chemical substance to be identified is determined to contain resource-recycled carbon based on the ratio ($R_2/R_1$). Specific examples of the discrimination step are shown below.

In the present invention, the ratio ($R_2/R_1$) can be used to determine whether the carbon raw material in the chemical substance to be identified contain resource-recycled carbon. Specifically, the ratio ($R_2/R_1$) is judged to be 0.5 or more and 2.0 or less, and the carbon raw material in the chemical substance to be identified is determined to contain resource-recycled carbon when the ratio ($R_2/R_1$) is 0.5 or more and 2.0 or less.

Note that the criterion for the ratio ($R_2/R_1$) is preferably 0.75 or more and 1.3 or less, more preferably 0.9 or more and 1.1 or less, and further preferably 0.95 or more and 1.05 or less, from the viewpoint of improving the determination accuracy.

Here, even if resource-recycled carbon, carbon derived from biomass resources, and carbon derived from fossil fuel resources are used as the carbon raw material, there is no difference in physical properties such as molecular weight, melting point, and mechanical properties. However, the carbon-14 content rates of chemical substances using resource-recycled carbon, carbon derived from biomass resources, and carbon derived from fossil fuel resources are each different.

Specifically, the chemical substances using resource-recycled carbon roughly match the carbon-14 content rates of standard chemical substances, as described above. The carbon derived from fossil fuel resources does not contain carbon-14, which has a half-life of 5,730 years, and therefore the content rate $R_2$ (%) of chemical substances using carbon derived from fossil fuel resources becomes lower. The carbon derived from biomass resources contains carbon-14, and therefore the content rate $R_2$ (%) of chemical substances using carbon derived from biomass resources becomes higher. In other words, the main carbon raw material in the chemical substance to be identified can be determined as resource-recycled carbon when the ratio ($R_2/R_1$) is 0.5 or more and 2.0 or less. In particular, all the carbon raw materials in the chemical substance to be identified can be determined as resource-recycled carbon when the ratio ($R_2/R_1$) is 1. A large amount of carbon derived from fossil fuel resources other than the resource-recycled carbon can also be determined to be mixed in as the chemical substance to be identified when the ratio ($R_2/R_1$) is less than 1. In addition, carbon derived from biomass resources other the resource-recycled carbon can be determined to be mixed in as the chemical substance to be identified when the ratio ($R_2/R_1$) is more than 1.

The ratio ($R_2/R_1$) is preferably 1 or more since it is preferable to use more carbon derived from biomass resources than carbon derived from fossil fuel resources, from the viewpoint of reducing the impact on the global environment. From the viewpoint of mainly resource-recycled carbon to reduce the impact on the global environment, a higher usage rate of resource-recycled carbon as a carbon raw material is suitable, and the ratio ($R_2/R_1$) is preferably 0.75 or more and 1.3 or less, more preferably 0.9 or more and 1.1 or less, and further preferably 0.95 or more and 1.05 or less.

<<Calculation of Usage Rate of Resource-Recycled Carbon>>

In the present invention, the ratio ($R_2/R_1$) of the content rate $R_2$ to the content rate $R_1$, obtained in the step S3, can also be used to calculate a usage rate of resource-recycled carbon in the carbon element of the chemical substance.

Specifically, the usage rate of resource-recycled carbon in the carbon element of the chemical substance can be calculated by $[100-|(R_2/R_1)-1|\times100]$ (%).

The usage rate of resource-recycled carbon in the carbon element of the chemical substance calculated by the formula can be displayed to show that the carbon element of the chemical substance contains resource-recycled carbon. The usage rate of resource-recycled carbon in the carbon elements of the chemical substances may be displayed on various goods, such as articles made from chemical substances, and on the packages of various goods. This can inform consumers whether a carbon element in a chemical substance is derived from resource-circulated carbon. Similarly, consumers can be clearly informed of the usage rate of resource-recycled carbon in the carbon element of the chemical substance.

Method for Producing Ethanol

Next, a method for producing ethanol as a standard chemical substance and ethanol as a chemical substance obtained from recycled raw materials will be described in detail. Such ethanol is preferably obtained by converting waste-derived gas with either a gas-assimilating microorganism or a metal catalyst. The waste-derived gas is preferably a synthesis gas containing carbon monoxide and hydrogen. A method for producing ethanol in a case where the waste-derived gas is a synthesis gas will be described in detail below.

The method for producing ethanol includes a raw material gas generation step, a synthesis gas purification step, an ethanol conversion step, and a purification step.

(Raw Material Gas Generation Step)

In the raw material gas generation step, gasification of waste can be done, for example, using a gasifier. The gasifier is a furnace that burns (incompletely burns) carbon sources, and examples thereof include a shaft furnace, a kiln, a fluid bed furnace, a gasification modified furnace. The temperature at which the waste is gasified into raw material gas is not limited, and is usually 100 to 2,500° C. and preferably 200 to 2,100° C.

The raw material gas obtained from the gasification of waste may contain carbon monoxide and hydrogen, and may also contain carbon dioxide, oxygen, and nitrogen. The raw material gas may further contain components such as soot, tar, nitrogen compounds, sulfur compounds, phosphorous compounds, organic compounds, and the like. The raw material gas typically contains 0.1% by volume or more and 80% by volume or less of carbon monoxide and 0.1% by volume or more and 80% by volume or less of hydrogen, and may contain 0.1% by volume or more and 70% by volume or less of carbon dioxide.

The raw material gas may be produced by carrying out heat treatment (commonly known as gasification) in which the waste is burned (incompletely burned), that is, by partially oxidizing the waste, as a gas containing 0.1% by volume or more, preferably 10% by volume, and more preferably 20% by volume of carbon monoxide, although there are no limitations.

(Synthesis Gas Purification Step)

The raw material gas may be made into synthesis gas by removing or reducing certain substances such as various pollutants, soot particles, impurities, and compounds in undesirable amounts as described above. In a case where ethanol is obtained from synthesis gas by microbial fermentation, it is preferable to reduce or remove substances that are undesirable for the stable cultivation of microorganisms and compounds in undesirable amounts from the raw material gas, so that the content of each component contained in the raw material gas is in a range suitable for the stable cultivation of microorganisms. In a case where ethanol is obtained from synthesis gas using a metal catalyst, substances that deactivate the metal catalyst may also be reduced or removed.

In the synthesis gas purification step, for example, the synthesis gas may be obtained by purifying the raw material gas through treatment using one or more of the following separators: a moisture separator composed of a gas chiller or the like; a low-temperature type (deep-cooling type) separator; a particulate separator that separates fine particles such as soot, represented by various filters such as cyclones and bag filters; a water-soluble impurity separator such as a scrubber; a desulfurization apparatus (sulfide separator); a membrane separation type separator; a deoxygenation apparatus: a pressure swing adsorption type separator (PSA); a temperature swing adsorption type separator (TSA); a pressure-temperature swing adsorption type separator (PTSA); a separator using activated carbon; and a separator using a deoxidizing catalyst, specifically, a copper catalyst or a palladium catalyst.

In a case where ethanol is obtained by microbial fermentation, it is preferable to reduce the concentration of carbon dioxide gas in the raw material gas. For example, it is preferable to reduce the concentration of carbon dioxide gas in the synthesis gas by using a pressure swing adsorption type separator filled with regeneration adsorbent containing a zeolite to adsorb carbon dioxide gas in the synthesis gas onto the regeneration adsorbent.

The resulting synthesis gas contains at least carbon monoxide and hydrogen as essential components as described above, and may further contain carbon dioxide and nitrogen. The concentration of carbon monoxide in the synthesis gas is usually 20% by volume or more and 80% by volume or less, preferably 25% by volume or more and 50% by volume or less, and more preferably 30% by volume or more and 45% by volume or less, with respect to the total concentration of carbon monoxide, carbon dioxide, hydrogen, and nitrogen in the synthesis gas.

The concentration of hydrogen in the synthesis gas is usually 10% by volume or more and 80% by volume or less, preferably 30% by volume or more and 55% by volume or less, and more preferably 30% by volume or more and 50% by volume or less, with respect to the total concentration of carbon monoxide, carbon dioxide, hydrogen, and nitrogen in the synthesis gas.

The concentration of carbon dioxide in the synthesis gas is not limited, and is usually 0.1% by volume or more and 40% by volume or less and preferably 0.3% by volume or more and 30% by volume or less, with respect to the total concentration of carbon monoxide, carbon dioxide, hydrogen and nitrogen in the synthesis gas. In a case where ethanol production is carried out from synthesis gas by microbial fermentation, it is particularly preferable to lower the concentration of carbon dioxide in the synthesis gas, and from such a viewpoint, the concentration of carbon dioxide is more preferably 0.5% by volume or more and 25% by volume or less.

The concentration of nitrogen in the synthesis gas is usually 40% or less, preferably 1% by volume or more and 40% by volume or less, and more preferably 5% by volume or more and 15% by volume or less, with respect to the total concentration of carbon monoxide, carbon dioxide, hydrogen, and nitrogen in the synthesis gas.

The concentration of carbon monoxide, carbon dioxide, hydrogen, and nitrogen in the synthesis gas can be set to a predetermined range by changing the burning conditions as appropriate, such as the type of waste, the gasification temperature in the raw material gas generation step, and the concentration of oxygen in the feed gas during gasification.

In a case where the concentration of carbon monoxide or hydrogen is required to change, for example, it is changed to waste with a high ratio of hydrocarbons (carbon and hydrogen), such as waste plastics, and in a case where the concentration of nitrogen is required to lower, a gas with a high concentration of oxygen can be supplied in the raw material gas generation step.

In addition, at least one of the raw material gases and the synthesis gas may be adjusted for the concentration of carbon monoxide, carbon dioxide, hydrogen, and nitrogen components as appropriate. For concentration adjustment, at least one of these components may be added to the raw material gas or the synthesis gas. The amount added is, for example, less than 50% by volume, preferably less than 30% by volume, and more preferably less than 10% by volume, with respect to the total amount of the raw material gas or the synthesis gas. However, in the case of producing standard chemical substances, carbon monoxide and carbon dioxide to be added need to be waste-derived gas.

(Ethanol Conversion Step)

The synthesis gas is converted to ethanol in the ethanol conversion step. The synthesis gas may be converted to ethanol by either a gas-assimilating microorganism or a metal catalyst as described above in the ethanol conversion step and is preferably converted by a gas-assimilating microorganism.

<<Ethanol Conversion by Microbial Fermentation>>

In a case where a gas-assimilating microorganism is used to convert synthesis gas to ethanol, the synthesis gas is supplied to a microbial fermenter and undergoes microbial fermentation in the microbial fermenter to produce ethanol. The microbial fermenter is preferably a continuous fermentation apparatus.

The microbial fermenter can be of any shape, including agitated, airlift, bubble tower, loop, open bond, and photobio types, but in the present invention a known loop reactor having the main tank part and a reflux part can be suitably used for the microbial fermenter.

For the synthesis gas supplied to the microbial fermenter, the synthesis gas obtained through the synthesis gas purification step described above may be used as synthesis gas as it is, or another predetermined gas may be added before supplying it. Examples of such another predetermined gas include at least one selected from the group consisting of sulfur compounds such as sulfur dioxide, phosphorus compounds, and nitrogen compounds.

Although synthesis gas and microorganism culture medium may be continuously supplied to the microbial fermenter, it is not necessary to supply synthesis gas and microorganism culture medium simultaneously, and synthesis gas may be supplied to the microbial fermenter to which microorganism culture medium has been supplied in advance. Certain anaerobic microorganisms are known to generate ethanol and the like from substrate gas such as synthesis gas by fermentation, and gas-assimilating microorganisms of such types are cultivated in a liquid medium. For example, a liquid medium and gas-assimilating bacteria can be supplied and housed in a microbial fermenter while the liquid medium is agitated in this state, and the synthesis gas may be supplied into the microbial fermenter. This allows the cultivation of the gas-assimilating bacteria in the liquid medium and the fermentation action to produce ethanol from the synthesis gas.

In the microbial fermenter, the temperature of the medium (culture temperature) adopted may be any temperature and can be preferably about 30 to 45° C., more preferably about 33 to 42° C., and further preferably about 36.5 to 37.5° C. The culture time is preferably 1 hour or more for continuous cultivation, more preferably 7 days or more, particularly preferably 30 days or more, and most preferably 60 days or more. Although the upper limit is not specifically set, the culture time is preferably 720 days or less and more preferably 365 days or less, from the viewpoint of regular maintenance of the equipment. The culture time means the time from the addition of inoculum to the culture tank to the time when the entire culture medium in the culture tank is discharged.

The microorganisms (species) contained in the microorganism culture medium are not limited as long as they are capable of producing ethanol by microbial fermentation of synthesis gas using carbon monoxide as the main raw material.

For example, the microorganisms (species) are preferably those that generate ethanol from synthesis gas by the fermentation action of gas-assimilating bacteria, and particularly preferably those that have a metabolic pathway for acetyl COA. Among the gas-assimilating bacteria, the genus *Clostridium* is more preferable and includes *Clostridium autoethanogenum, Clostridium ljungdahlii, Clostridium aceticum, Clostridium carboxidivorans, Moorella thermoacetica*, and *Acetobacterium woodii*. Among these, *Clostridium autoethanogenum* is particularly preferable.

The medium used for cultivating the microorganisms (species) described above is not particularly limited as long as the composition is appropriate for bacteria, and is a liquid containing water as the main component and nutrients (for example, vitamins, phosphoric acid, or the like) dissolved or dispersed in the water. The composition of such a medium is adjusted so that gas-assimilating bacteria can grow well. For example, a medium in a case where the genus *Clostridium* is used as the microorganisms can be referenced to [0097] to [0099] of US 2017-260552 A or the like.

<<Separation Step of Ethanol Conversion by Microbial Fermentation>>

A culture medium containing ethanol (ethanol-containing culture medium) is obtained by microbial fermentation. The ethanol-containing culture medium is then subjected to a separation step.

In the separation step, for example, the ethanol-containing culture medium may be heated to 23 to 500° C. under the condition of 0.01 to 1,000 kPa (absolute pressure) to separate the liquid or solid components containing microorganisms from the gaseous components containing ethanol. By implementing such a separation step, foaming does not occur in the distillation apparatus in the distillation operation during the separation and purification of ethanol, which will be described later, so that the distillation operation can be continuously carried out. In addition, ethanol can be separated and purified efficiently during the separation and purification, which will be described later.

In the separation step, the ethanol-containing culture medium is heated preferably under the condition of 10 to 200 kPa, more preferably under the condition of 50 to 150 kPa, and further preferably under ambient pressure, preferably at a temperature of 50 to 200° C., more preferably at a temperature of 80° C. to 180° C., and at a temperature of further preferably 100 to 150° C., from the viewpoint of efficiently separating the liquid or solid components containing microorganisms, their carcasses, proteins derived from microorganisms, or the like from the gaseous components containing ethanol.

The gaseous components containing ethanol obtained in the separation step may be liquefied by condensation to form an ethanol-containing liquid. The apparatus used in the liquefaction step is not limited and is preferably a heat exchanger, particularly a condenser. Examples of the condenser include a water-cooled type, an air-cooled type, and an evaporative type, and among them, the water-cooled type is preferable. The condenser may comprise one stage or a plurality of stages.

In the separation step, the solid components containing microorganisms and the liquid components containing ethanol (ethanol-containing liquid) may be separated by a solid-liquid separator such as a filter apparatus for solid-liquid separation, instead of separating the liquid or solid components containing microorganisms from the gaseous components containing ethanol as described above.

<<Ethanol Conversion by Metal Catalyst>>

Ethanol may also be produced from synthesis gas using a metal catalyst, as described above. The metal catalyst may include a hydrogenation active metal or an aggregate of a hydrogenation active metal and an auxiliary active metal.

The hydrogenation active metal may be any metal conventionally known to be capable of synthesizing ethanol from gas mixtures, and examples thereof include alkali metals such as lithium and sodium, elements belonging to Group 7 of the periodic table such as manganese and rhenium, elements belonging to Group 8 of the periodic table such as ruthenium, elements belonging to Group 9 of the periodic table such as cobalt and rhodium, and elements belonging to Group 10 of the periodic table such as nickel and palladium.

These hydrogenation active metals may be used singly or in combination of two or more. The hydrogenation active metal is preferably a combination of rhodium or ruthenium with an alkali metal and other hydrogenation active metals, such as a combination of rhodium, manganese and lithium, or a combination of ruthenium, rhenium and sodium, from the standpoint of further improving CO conversion rates and improving ethanol selectivity.

Examples of auxiliary active metals include titanium, magnesium, and vanadium. Such auxiliary active metals are supported in addition to the hydrogenation active metals, thereby enhancing the CO conversion rates and ethanol selectivity.

The metal catalyst is preferably a rhodium-based catalyst. The rhodium-based catalyst may be used in combination with metal catalysts other than the rhodium-based catalyst. Such other metal catalysts include copper alone or a catalyst in which copper and a transition metal other than copper are supported on a carrier.

In a case where a metal catalyst is used, a product containing acetaldehyde and acetic acid is usually obtained in addition to ethanol, and thus it is preferable to remove the product through an ethanol purification step such as distillation.

(Purification Step)

After the ethanol conversion step, a purification step may be carried out to further purify the ethanol-containing liquid. In a case where the ethanol-containing liquid obtained by microbial fermentation has already been removed of microorganisms and other components, the purification step may be carried out without undergoing the separation step described above.

The purification step is a step of separating the ethanol-containing liquid into a distillate with a higher concentration of ethanol and a canned liquid with a lower concentration of ethanol. Examples of apparatuses used in the purification step include distillation apparatuses, treatment apparatuses containing osmotic evaporating membranes, treatment apparatuses containing zeolite membranes, treatment apparatuses for removing substances with a low boiling point lower than that of ethanol, treatment apparatuses for removing substances with a high boiling point higher than that of ethanol, and treatment apparatuses containing ion exchange membranes. These apparatuses may be used alone, or in combination of two or more. As a unit operation, a distillation apparatus or membrane separation can be suitably used, and a distillation apparatus is more preferable. Further, as the membrane separation, a zeolite membrane can be suitably used.

In a case where a distillation unit is used, heating distillation is carried out. In the heating distillation, the desired ethanol can be obtained as a distillate with high purity. The temperature in the distillation apparatus during the distillation of ethanol is not limited and is preferably 110° C. or lower, and more preferably about 70 to 105° C. By setting the temperature in the distillation apparatus to the above range, separation of ethanol from other components, that is, distillation of ethanol can be carried out more reliably.

In the heating distillation, an ethanol-containing liquid is introduced into a distillation apparatus equipped with a heater using steam of 100° C. or higher to raise the temperature at the bottom of the distillation column to 90° C. or higher within 30 minutes, and then the ethanol-containing liquid may be introduced from the middle of the distillation column. Further, in the heating distillation using a distillation apparatus, it is preferable to carry out the distillation step within ±15° C. in the temperature difference among the bottom, middle, and top of the column. When the temperature difference is within ±15° C., it is easier to obtain high purity ethanol. The distillation temperature difference is preferably 13° C., and more preferably ±11° C. With these distillation temperature differences, separation of ethanol from other components, that is, purification by distillation of ethanol can be carried out more reliably.

The pressure in the distillation apparatus during the distillation of ethanol may be ambient pressure, but is preferably less than atmospheric pressure, and more preferably about 60 to 95 kPa (absolute pressure). By setting the pressure in the distillation apparatus in the above range, the separation efficiency of ethanol can be improved, and thus the yield of ethanol can be improved.

Method for Generating Ethylene

Next, a method for producing ethylene as a standard chemical substance and ethylene as a chemical substance obtained from recycled raw materials will be described in detail.

Ethanol using resource-recycled carbon produced by the production method as a carbon raw material is converted to ethylene by the ethylene generation step, thereby obtaining an ethylene-containing product. Specifically, ethanol may be brought into contact with a catalyst to be converted into ethylene. Ethanol is converted to ethylene by a dehydration reaction.

The catalysts used for the generation of ethylene is not limited as long as they are catalysts capable of converting ethanol into ethylene, and include zeolites, modified zeolites such as P-modified zeolites, silica-alumina, alumina, silicified, titanated, zirconated, or fluorinated alumina, acid catalysts such as silicoaluminophosphate (hereinafter, these may be collectively referred to as "zeolite or alumina-based catalysts"), and heteropolyacid-supported catalysts.

As zeolites, those containing at least one type of 10-membered ring in their structure are advantageous and have microporous materials consisting of silicon, aluminum, oxygen, and boron as optional components, and specific examples thereof include MFI (ZSM-5, silicalite-1, boralite C, TS-1), MEL (ZSM 11, silicalite-2, boralite D, TS-2, SSZ-46), FER (ferrierite, FU-9, ZSM-35), MTT (ZSM-23), MWW (MCM-22, PSH-3, ITQ-1, MCM-49), TON (ZSM-22, Theta-1, NU-10) EUO (ZSM-50, EU-1), MFS (ZSM-57), and ZSM-48.

The zeolites are preferably zeolite with a Si/Al ratio of 10 or more. The zeolite with a Si/Al ratio of 10 or more preferably has a Si/Al ratio of 100 or more, and preferably contains at least one selected from the group consisting of MFI and MEL.

The zeolite is also preferably a dealuminated zeolite. For the dealuminated zeolite, it is advantageous to remove about 10% by mass of aluminum. This dealumination is advantageously carried out by steam treatment, followed by leaching if necessary.

For the zeolite and the dealuminated zeolite, it is advantageous to be basically of the H-type. They can also contain a metal compensating ion, such as at least one selected from the group consisting of Na, Mg, Ca, La, Ni, Ce, Zn, Co, as a sub-component (about 50% or less of the component).

The zeolite is mixed with a binder, preferably an inorganic binder, and formed into the desired shape, such as s pellet shape. The binder to be chosen has durability against temperature used in the dehydration process of the present invention and other conditions. The binder is at least one inorganic material selected from the group consisting of clay, silica, metal silicate, metal oxide (for example, $ZrO_2$), and a gel containing a mixture of silica and metal oxide.

The P-modified zeolite is a phosphorus-modified zeolite. In the ethylene generation step, it is also preferable to use the P-modified zeolite. The phosphorus modified zeolite can be produced on the basis of, for example, a zeolite having micropores with a Si/Al ratio as an initial atom ratio of 4 to 500 and specifically MFI, MOR, MEL, clinoptilolite, FER, MWW, TON, EUO, MFS, ZSM-48, or the like. The Si/Al ratio as the initial atom ratio is preferably 100 or less and more preferably 4 to 30. The P-modified zeolite in this production method can also be obtained on the basis of an inexpensive zeolite with a low Si/Al ratio (of 30 or less).

The P-modified zeolite can also be further modified with at least one metal selected from the group consisting of Mg, Ca, La, Ni, Ce, Zn, Co, Ag, Fe, and Cu.

A phosphorus-atom content rate of the P-modified zeolite is advantageously at least 0.05% by mass, and preferably 0.3 to 7% by mass.

In addition, for the zeolite as the raw material, it is advantageous that at least 10% by mass of aluminum is extracted and removed from the zeolite by leaching.

The catalyst using the P-modified zeolite may be the P-modified zeolite itself as a catalyst or may be a blended-type P-modified zeolite that combines the P-modified zeolite with other materials. The blended type can improve the hardness or catalytic activity of the catalyst.

Materials that can be mixed with the P-modified zeolite include various inert or catalytically active materials, or various binder materials, and specifically include kaolin and other clay-like compositions, rare earth metals in various forms, phosphates, alumina or alumina sol, titania, zirconia, quartz, silica or silica sol, and mixtures thereof. These components are effective in increasing the compressive strength of the catalyst and the blended catalyst. The catalyst can be formed into pellets and spheres, extruded into other shapes, or made into spray-dried particles. The amount of P-modified zeolite in the final catalyst product is 10 to 90% by mass and preferably 20 to 70% by mass, of all catalysts.

A suitable example of the P-modified zeolite is silicoaluminophosphate and more preferably silicoaluminophosphate of the AEL group, whose representative example is SAPO-11. The SAPO-11 is based on ALPO-11 and has an Al/P ratio of basically 1 atom/atom. The insertion of silicon into the ALPO framework by the addition of a silicon precursor during synthesis creates acid sites on the surface of the micropores of the zeolite with 10-membered rings. The content of silicon is 0.1 to 10% by atom (Al+P+Si is 100).

It is also preferable to use alumina as a catalyst in the ethylene generation step. Further, it is also preferable to use silicified, zirconated, titanated, or fluorinated alumina.

Alumina is generally characterized by having a wide range of acid strength distribution and Lewis- and Bronsted-type acid sites. Active alumina may be used as the alumina.

Alumina is also preferable to improve the selectivity of the catalyst by depositing silicon, zirconium, titanium, fluorite, and the like. In other words, the selectivity of the catalyst may be improved by silicification, zirconation, or titanation. Suitable commercially available alumina, preferably eta or gamma alumina having a surface area of 10 to 500 $m^2/g$ and an alkali content of 0.5% or less may be used for the production of such catalysts. The preparation may also be made by adding silicon, zirconium, and titanium at a total of 0.05 to 10% by mass. The addition of these metals may be carried out at the time of producing alumina, or these metals can be added to the alumina after production and may also be added in the form of precursors. Also, fluorinated alumina itself is known and can be produced according to conventional techniques.

In the ethylene generation step, it is also preferable to use a heteropolyacid-supported catalyst. The heteropolyacid-supported catalyst contains a heteropolyacid supported on a suitable catalyst carrier. The term "heteropolyacid" refers to a heteropolyacid compound in the form of a free acid or in the form of a heteropolyacid salts, such as an alkali metal salt, an alkaline earth metal salt, an ammonium salt, a bulky cation salt, and/or a metal salt (in these cases, the salt may be either a complete salt or a partial salt).

The anions of heteropolyacids typically contain 12 to 18 oxygen-bonded polyvalent metal atoms, known as peripheral atoms, surrounding one or more central atoms in a symmetrical manner. The peripheral atoms are appropriately selected from the group consisting of molybdenum, tungsten, vanadium, niobium, tantalum, and combinations thereof. The central atoms are preferably silicon or phosphorus. The central atoms may include any one of atoms selected from the group consisting of Groups I to VIII in the periodic table of elements, such as copper, beryllium, zinc, cobalt, nickel, boron, aluminum, gallium, iron, cerium, arsenic, antimony, bismuth, chromium, rhodium, silicon, germanium, tin, titanium, zirconium, vanadium, sulfur, tellurium, manganese nickel, platinum, thorium, hafnium, tellurium and iodine. Suitable heteropolyacids include Keggin, Wells-Dawson, and Anderson-Evans-Perloff heteropolyacids.

The heteropolyacid component of the heteropolyacid-supported catalyst is preferably a heteropolytungstic acid, which is a heteropolyacid whose peripheral atom is a tungsten atom. Preferable heteropolytungstic acids are any those with Keggin or Wells-Dawson structure as the main component.

Examples of suitable heteropolytungstic acids include 18-phosphotungstic acid ($H_6[P_2W_{18}O_{62}]\cdot xH_2O$), 12-phosphotungstic acid ($H_3[PW_{12}O_{40}]\cdot xH_2O$), 12-silicotungstic acid ($H_4[SiW_{12}O_{40}]\cdot xH_2O$), cesium hydrogen silicotungstate ($Cs_3H[SiW_{12}O_{40}]\cdot xH_2O$), monopotassium phosphotungstate ($KH_5[P_2W_{18}O_{62}]\cdot xH_2O$), monosodium 12-silicotungstic acid ($NaK_3[SiW_{12}O_{40}]\cdot xH_2O$), and potassium phosphotungstate ($K_6[P_2W_{18}O_{62}]\cdot xH_2O$). A mixture of two or more different heteropolytungstic acids and salts can be also used.

The heteropolyacid component of the heteropolyacid-supported catalyst is more preferably selected from the group consisting of silicotungstic acid, phosphotungstic acid, and a mixture thereof, such as 12-silicotungstic acid ($H_4[SiW_{12}O_{40}]\cdot xH_2O$), 12-phosphotungstic acid ($H_3[PW_{12}O_{40}]\cdot xH_2O$), and a mixture thereof. The heteropolyacid acid is further preferably silicotungstic acid and most preferably 12-silicotungstic acid.

The molecular weight of the heteropolyacid is preferably more than 700 and less than 8,500, and more preferably more than 2,800 and less than 6,000. Such heteropolyacids also include these dimerization complexes.

The catalyst carrier used in the heteropolyacid-supported catalyst may be any suitable catalyst carrier known in the art. Raw materials suitable for the catalyst carrier include mordenite (for example, montmorillonite), clay, bentonite, diatomaceous earth, titania, active carbon, alumina, silica, silica-alumina, silica-titania cogel, silica-zirconia cogel, carbon coated alumina, zeolite, zinc oxide, and flame pyrolysis oxide. The catalyst carrier preferably contains a silica gel carrier and a carrier produced by flame hydrolysis of $SiCl_4$ as the main components.

The shape of the catalyst carrier is not limited and may be, for example, in powder form, granular form, pelletized form, spherical form, or extruded form.

Ethanol is not limited but is preferably converted to ethylene by contacting the catalyst in the gas phase. Further, ethanol may be mixed with water, and optional components may also be mixed as appropriate in addition to ethanol and water. One or both of the water and optional components may be contacted with a catalysis as together with ethanol as a gas.

The catalyst is, for example, filled in a reaction vessel, and ethanol or at least one selected from ethanol, water, and other optional components may be supplied as a gas to the reaction vessel filled with the catalyst. The gas-phase dehydration reaction may be performed to discharge an ethylene-containing product from the reaction vessel in the gas phase. In a case where ethanol remains in the gas discharged from the reaction vessel, a component containing the ethanol may be separated from the ethylene-containing product, and the component containing the ethanol may be supplied to the reaction vessel again.

In the case of a zeolite or alumina-based catalyst, the temperature of the reaction vessel is, for example, 280 to 600° C., preferably 300 to 550° C., and more preferably 330 to 530° C. The pressure (absolute pressure) of the reaction vessel is, for example, 50 kPa to 3 MPa, preferably 50 kPa to 1 MPa, and further preferably 0.12 MPa to 0.65 MPa.

In the case of a heteropolyacid-supported catalyst, the temperature of the reaction vessel is, for example, 170° C. or higher, preferably within the range of 180 to 270° C., more preferably within the range of 190 to 260° C., and further preferably within the range of 200 to 250° C. The pressure of the reaction vessel is preferably within the range of 0.1 to 4.5 MPa, more preferably 1.0 to 3.5 MPa, and further preferably 1.0 to 2.8 MPa.

Note that in the case of a heteropolyacid-supported catalyst, the heteropolyacid-supported catalyst may be heated to a temperature of 220° C. or higher and kept at that temperature for a sufficient time before contacting with ethanol to remove bound water from the heteropolyacid component of the heteropolyacid-supported catalyst.

Method for Producing Polymer

Next, a method for producing a polymer having the constituent unit derived from ethylene described above as a chemical substance obtained from a recycled raw material will be described.

The polymer comprising the constituent unit derived from ethylene described above can be obtained by polymerizing the monomer containing ethylene described above. The polymer may be homopolyethylene obtained by polymerizing ethylene alone, or may be a copolymer obtained by polymerizing ethylene and a monomer component other than ethylene.

The polymer is preferably a polyethylene resin such as low-density polyethylene (LDPE), high-density polyethylene (HDPE), linear low-density polyethylene (LLDPE), and ultra-high-molecular-weight polyethylene (UHMWPE).

Further, any polymer comprising the constituent unit derived from ethylene described above may be used, and for example, the polymer may be a copolymer of ethylene such as ethylene-vinyl acetate copolymer (EVA), ethylene-methyl acrylate copolymer, ethylene-ethyl (meth)acrylate copolymer, ethylene (meth)acrylate copolymer, ethylene propylene rubber (EPM), and ethylene-propylene-diene rubber (EPDM), and a monomer other than ethylene.

The low-density polyethylene has a short-chain branch and a long-chain branch in the molecular structure, and has a density of 0.910 g/cm³ or more and less than 0.942 g/cm³, and typically a density of 0.930 g/cm³ or less. Polyethylene having a density of 0.930 g/cm³ or more and less than 0.942 g/cm³ may be referred to as medium-density polyethylene. The high-density polyethylene is polyethylene having few branches in the molecular structure and a density of 0.942 g/cm³ or more.

The linear low-density polyethylene is generally a copolymer of ethylene and a small amount of an α-olefin other than ethylene, and examples of the α-olefin other than ethylene include an α-olefin having 3 to 10 carbon atoms and specifically include propylene, butene-1, pentene-1, 4-methyl-pentene-1, hexene-1, octene-1, and decene-1. The density of the linear low-density polyethylene is less than 0.942 g/cm³ and typically 0.930 g/cm³ or less, and for example 0.880 g/cm³ or more and typically 0.910 g/cm³ or more.

The ultra-high-molecular-weight polyethylene (UHMWPE) is a polyethylene with a higher molecular weight than ordinary polyethylene, and for example, is a polyethylene resin having a weight-average molecular weight of 400,000 or more and preferably a weight-average molecular weight of 1 million or more. The ultra-high-molecular-weight polyethylene (UHMWPE) has a good mechanical strength in various applications as the weight-average molecular weight increases. Further, the weight-average molecular weight of the ultra-high-molecular-weight polyethylene (UHMWPE) is preferably 7 million or less and further preferably 4 million or less from the viewpoint of ease of polymerization. Note that the weight-average molecular weight is a weight-average molecular weight in terms of standard polystyrene measured by gel permeation chromatography (GPC).

The ultra-high-molecular-weight polyethylene (UHMWPE) may be an ethylene homopolymer or may be a copolymer of ethylene and an α-olefin other than ethylene. The α-olefin other than ethylene are as described in the linear low-density polyethylene (LLDPE).

Ethylene can be made into a polyethylene resin in polymerization in the presence of a radical initiator, for example. The radical initiators include, but are not limited to, oxygen-based initiators such as organic peroxide, peroxyester, dialkyl peroxide, or combination thereof. Specific examples of the radical initiators include, but are not limited to, t-butyl peroxypivalate, di-t-butyl peroxide (DTBP), t-butyl peroxyacetate (TBPO), t-butyl peroxy-2-ethyl hexanoate, t-butyl peroxyneodecanoate (PND), t-butyl peroxyoctoate, and any combination of two or more thereof.

Ethylene can also be made into a polyethylene resin in polymerization in the presence of a catalyst such as a redox catalyst. Examples of the redox catalyst include a Ziegler-Natta catalyst, a metallocene catalyst, a Phillips catalyst, and a standard catalyst.

As the Ziegler-Natta catalyst, for example, triethylaluminum-titanium tetrachloride solid composite is used. The Ziegler-Natta catalyst may, for example, be used in combination with a titanium trichloride composition obtained by reducing titanium tetrachloride with an organic aluminum compound and further treating it with various electron donors and electron receptors, an organic aluminum compound, and an aromatic carboxylate, or as a supported catalyst by contacting magnesium halide with titanium tetrachloride and various electron donors.

Examples of the metallocene catalysts include compounds such as bis(cyclopentadienyl) metal complex having a structure in which a transition metal is sandwiched between π-electron unsaturated compounds. Specific examples thereof include compounds in which one or two or more cyclopentadienyl rings or analogs thereof are present as ligands in tetravalent transition metals such as titanium, zirconium, nickel, palladium, hafnium, and platinum.

The Ziegler-Natta catalyst and the metallocene catalyst may be each used in combination with specific cocatalysts (promoters). Specific examples of the cocatalysts include methylaluminoxane (MAO) and boron-based compounds.

The Phillips catalysts are, for example, catalytic systems containing a chromium compound such as chromium oxide, and specific examples thereof include catalysts in which chromium compounds such as chromium trioxide and chromate ester are supported on solid oxides such as silica, alumina, silica-alumina, and silica-titania.

The standard catalyst is a known catalyst using molybdenum oxide and includes, for example, gamma-alumina molybdenum oxide.

When using a radical initiator, a method of polymerizing ethylene includes a high pressure method. In the high pressure method, ethylene may be polymerized in an environment of 1,000 to 4,000 atm and 100 to 350° C., for example, with a multistage gas compressor. The residual monomer is then separated and cooled to obtain ethylene. Ethylene can be produced by a high pressure method to produce low-density polyethylene (LDPE).

When using catalysts such as Ziegler-Natta catalyst, metallocene catalyst, Phillips catalyst, and standard catalyst, the polymerization of ethylene may be carried out in a low pressure method or a medium pressure method. When using these catalysts, the polymerization of ethylene is preferably carried out in a liquid-phase polymerization method, a gas-phase polymerization method, or a suspension polymerization method. HDPE can be produced by polymerizing ethylene using these catalysts in a low pressure method or a medium pressure method. Linear low-density polyethylene (LLDPE) can be also produced by copolymerizing ethylene with a small amount of α-olefin other than ethylene using these catalysts. Further, ultra-high-molecular-weight polyethylene (UHMWPE) can be obtained by carrying out polymerization for a long period of time by a low-pressure suspension polymerization method.

The invention claimed is:

1. A method for determining whether a main chemical substance comprises a resource-recycled carbon, the method comprising:

providing a standard chemical substance having carbon element in which carbon has been recycled as a resource;

measuring a carbon-14 content rate Ri of the standard chemical substance having carbon element in which carbon has been recycled as a resource, the carbon-14 content rate $R_1$ being measured by a method selected from the group consisting of liquid scintillation counting, gas proportional counting, and accelerator mass spectrometry, wherein the content rate $R_1$ is an average value of carbon-14 content rates of a plurality of standard chemical substances;

providing a chemical substance to be identified, the chemical substance to be identified being selected from the group consisting of ethanol, a polymer having a constituent unit derived from ethylene, butadiene, propylene, isobutene, acetaldehyde, acetic acid, ethyl acetate, methyl (meth)acrylate, ethyl-t-butyl ether ethylene glycol, an ester composition, an acrylic acid, an aminohexanoic acid, diethyl carbonate, a polyester resin, a polyethylene resin (PE), a polyethylene terephthalate resin (PET), a polypropylene resin (PP), a polyisobutylene resin, a polymethyl methacrylate resin (PMMA), ethylene-propylene-diene rubber (EPDM), a polybutylene terephthalate resin (PBT), a polyethylene furanoate resin (PEF), and a polyurethane resin (PU);

measuring a carbon-14 content rate $R_2$ of the chemical substance to be identified, the carbon-14 content rate $R_2$ being measured by a method selected from the group consisting of liquid scintillation counting, gas proportional counting, and accelerator mass spectrometry;

calculating a ratio ($R_2/R_1$) of the content rate $R_2$ to the content rate $R_1$; and determining that the chemical substance to be identified contains resource-recycled carbon from the ratio ($R_2/R_1$), wherein the chemical substance to be identified contains resource-recycled carbon when a ratio ($R_2/R_1$) is 0.5 or more and 2.0 or less; and producing one or more selected from the group consisting of ethanol, ethylene, and a polymer from the chemical substance to be identified responsive to determining that the chemical substance to be identified contains resource-recycled carbon.

2. The method according to claim 1, wherein the carbon raw material in the chemical substance to be identified comprises the resource-recycled carbon when the ratio ($R_2/R_1$) is 1.0.

3. The method according to claim 1, wherein the standard chemical substance is ethanol.

4. The method according to claim 1, wherein the chemical substance to be identified is one chosen from the group consisting of ethylene and polyethylene resins.

5. The method according to claim 1, wherein the average value of carbon-14 content rates of a plurality of the standard chemical substances is an average value of carbon-14 content rates of the standard chemical substances produced at a plurality of sites.

6. The method according to claim 1, wherein the average value of carbon-14 content rates of a plurality of the standard chemical substances is an average value of carbon-14 content rates of the standard chemical substances produced in a plurality of times.

7. The method according to claim 1, wherein the content rate $R_1$ is a carbon-14 content rate of each production lot in which the standard chemical substance is produced from resource-recycled carbon.

8. The method according to claim 1, comprising a step of calculating [100−|($R_2/R_1$)−1|×100] (%) as a usage rate of the resource-recycled carbon.

9. The method according to claim 1, wherein the ethanol is produced from the chemical substance to be identified responsive to determining that the chemical substance to be identified contains resource-recycled carbon.

10. The method according to claim 1, wherein the ethylene is produced from the chemical substance to be identified responsive to determining that the chemical substance to be identified contains resource-recycled carbon.

11. The method according to claim 1, wherein the polymer is produced from the chemical substance to be identified responsive to determining that the chemical substance to be identified contains resource-recycled carbon.

* * * * *